United States Patent
Thompson (12)

(10) Patent No.: US 7,498,039 B2
(45) Date of Patent: Mar. 3, 2009

(54) NUTRITIONAL SUPPLEMENT CONTAINING SEA WATER MINERALS

(76) Inventor: Diana F. Thompson, 2973 Byron Center Ave. SW. - Apt. 2, Wyoming, MI (US) 49509

(*) Notice: Subject to any disclaimer, the term of this patent is extended or adjusted under 35 U.S.C. 154(b) by 875 days.

(21) Appl. No.: 10/683,336

(22) Filed: Oct. 10, 2003

(65) Prior Publication Data
US 2004/0076687 A1    Apr. 22, 2004

Related U.S. Application Data

(60) Provisional application No. 60/417,746, filed on Oct. 10, 2002.

(51) Int. Cl.
*A61K 9/08* (2006.01)
(52) U.S. Cl. .................................................. 424/400
(58) Field of Classification Search ................. None
See application file for complete search history.

(56) References Cited

U.S. PATENT DOCUMENTS 4,649,050 A * 3/1987 Veech .......................... 424/601

* cited by examiner

*Primary Examiner*—Caros A. Azpuru
(74) *Attorney, Agent, or Firm*—Ian C. McLeod

(57) ABSTRACT

A nutritional supplement composition for humans, animals, and plants is provided which comprises sea water elements and minerals in substantially the same proportion as in natural sea water or sea water and a caloric nutrient source. Preferably, the composition comprises the sea water elements and minerals or sea water in an isotonic solution with a carbohydrate source. The composition preferably further includes dextrose and optionally, protein hydrolyzates, vitamins, and other nutritionally or pharmaceutically acceptable compositions. The composition is administered orally or parentally, in particular, intravenously or intramuscularly.

13 Claims, No Drawings

US 7,498,039 B2

NUTRITIONAL SUPPLEMENT CONTAINING SEA WATER MINERALS

CROSS-REFERENCE TO RELATED APPLICATION

This application claims the benefit of Provisional Patent Application No. 60/417,746 filed Oct. 10, 2002.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not Applicable.

BACKGROUND OF THE INVENTION (1) Field of the Invention

The present invention relates to a nutritional composition comprising sea water elements and minerals in substantially the same proportion as in natural sea water or sea water and a caloric nutrient source, preferably a simple sugar or other easily metabolizable carbohydrate. The composition is useful for providing the sea water minerals to a human, animal, or plant. Preferably, the composition comprises the sea water elements and minerals or sea water in an isotonic solution. The composition preferably further includes dextrose and optionally, protein hydrolyzates, vitamins, and other nutritionally or pharmaceutically acceptable compositions. The composition is administered orally or parentally, in particular, intravenously or intramuscularly.

(2) Description of Related Art

Throughout recorded history, sea water has been extolled in folklore for its healing and curative properties. To this very day, sea water is used by various peoples as a cure for a variety of skin conditions. In general, the skin conditions are treated by immersing the skin in a bath containing sea water or a concentrated solution of sea water minerals prepared from crystalline salts, e.g., foot baths. It has been suggested that the high salt concentration and high osmolality of sea water may be responsible for its healing power. However, notwithstanding the thousands of years of folklore extolling the healing powers of sea water and the several world renown spas that provide sea water therapies, modern medical science has been slow to investigate what attributes in sea water might provide the foundation for the folklore claims to its healing powers. As a consequence, sea water remains nothing more than a folk remedy and its healing powers for the most part have been met with skepticism.

Despite modern medical science's general disinterest in the healing powers of sea water, from time to time treatments using sea water as an ingredient have been proffered. For the most part, these treatments have been limited to topical uses of sea water. For example, U.S. Pat. No. 4,582,226 to Dillon discloses a treatment for sensitive animal tissue such as ulcerated tissue using specially prepared sea water. The sea water is prepared by removing debris and small organisms, sterilizing, and diluting to provide a sterilized solution with an osmolality and an isotonicity compatible with the animal tissue. Dillon does not disclose parenterally or orally administered treatments using the specially prepared sea water.

Another topical treatment comprising sea water is disclosed in U.S. Pat. No. 5,084,281 to Dillon. This patent discloses a method and solution for the topical treatment of tissue wounds with sea water. The solution comprises a salt and mineral solution having the characteristics of sea water to which is added a chlorinergic agent to stimulate local vasodilation and neurologic function. Dillon does not disclose parenterally or orally administered treatments using the solution.

A series of patents by Commin disclose antiviral treatments which in particular embodiments contain sea water. For example, Australian Patent 612228 to Commin discloses an aqueous solution for the treatment of viral diseases such as HIV comprising white vinegar and mineral salts which can be provided by sea water. Preferably, the white vinegar and sea water are mixed 50:50. Commin discloses that the solution may be administered parenterally, in particular, by I.V. or I.M. injection, in which case the solution is suitably buffered or diluted, or both, so as to be isotonic to blood plasma.

International Patent WO 9627383 to Commin discloses an antiviral solution consisting of acetic acid and coconut powder extracts, a solution of mineral salts which can be provided by sea water, and extracts of cactaceae, liliaceae, anacardiaceae, and euphorbiaceae. The solution may be administered by injection in a form that is isotonic to blood plasma. The sea water is a convenient source of sodium, chlorides, sulfates, potassium, calcium, magnesium, and carbonates and bicarbonates.

Sea water has been used as a source of elements and minerals for plant fertilizers. For example, U.S. Pat. No. 4,015,971 to Barannik discloses a method for preparing fertilizers from sea water using iron ions. The iron ions form an iron hydroxide in the sea water which absorbs micro-elements and organic substances in the water and precipitates therewith. The precipitate contains about 24 to 31.5% iron and is used as a fertilizer.

Even though sea water has been used as a component of various medical treatments, the prior art does not disclose the use of sea water or the minerals thereof preferably in substantially same proportions as they occur in sea water per se as a nutritional supplement to provide sea water minerals to humans, animals, or plants to maintain or enhance health or as a treatment for viral or bacterial diseases.

SUMMARY OF THE INVENTION

The present invention provides a nutritional composition which comprises sea water elements and minerals in substantially the same proportion as in natural sea water or sea water and a caloric nutrient source, preferably a simple sugar or other easily metabolizable carbohydrate. The composition is useful for providing the sea water elements and minerals to a human, animal, or plant. Preferably, the composition comprises the sea water minerals or sea water in an isotonic solution and a carbohydrate source. The composition preferably further includes dextrose as the nutrient source and optionally, protein hydrolyzates, vitamins, and other nutritionally or pharmaceutically acceptable compositions. The composition is administered orally or parentally, in particular, intravenously or intramuscularly. The composition has antiviral and antibacterial properties and, therefore, is useful for the treatment of viral and bacterial diseases.

The term "sea water" includes water obtained from the oceans or seas or water to which the elements and minerals of the sea water are added. By way of example, sea water includes water from the Atlantic, Arctic, Antarctic, Pacific, and Indian Oceans; the Mediterranean, Carribean, North, Black, Sargasso, and Dead Seas. "Sea water" further includes water to which elements and minerals which had been isolated from sea water (e.g., sea salt) by gentle evaporation, which substantially maintains the proportion of the elements and minerals of the sea water, have been added and further includes water to which certified ultrapure elements and minerals have been added in proportions substantially similar to their proportions in sea water.

The term "sea water elements and minerals" refers to the elements and minerals obtained from sea water by gentle evaporation which substantially maintains the proportion of the elements and minerals of the sea water. "Sea water elements and minerals also refers to a mixture of elements and minerals prepared from certified ultrapure elements and minerals wherein the proportion of elements and minerals in the mixture are substantially the same as the proportion of the elements and minerals in natural sea water.

The term "simple sugars" by way of example includes but is not limited to saccharides such as sucrose, dextrose, glucose, lactose, maltose, galactose, arabinose, mannose, ribose, xylose, and fructose. Many of these simple sugars can be prepared from sugar cane, sugar beets, corn syrup, honey, and pureed fruits and vegetables.

The term "carbohydrate" refers to macronutrients which upon digestion yield glucose and other monosaccharides. By way of example, "carbohydrates" include starch, maltodextrin, and hydrolyzed cereal solids.

The term "protein hydrolyzates" refers to mixtures of proteins, peptides and amino acids prepared from proteins which by way of example includes soy, whey, casein, fibrin, egg albumin, and beef puree. Thus, protein hydrolyzates include but are not limited to hydrolyzed fibrin, casein, soy, whey, and meat.

The term "vitamins" includes by way of example the generally recognized vitamins A, $B_1$ (thiamin), $B_2$ (riboflavin), $B_6$ (pyridoxin), $B_{12}$ (colbalamins), C (ascorbic acid), D, E, and K ($K_1$ and $K_2$), folic acid, biotin, niacin. Vitamins further includes provitamins such as betacarotenoids.

The term "nutrient source" includes a compound or element which is important to the quality of the cellular functions of the human or animal.

In the present invention, these solutions when administered enable the cells of the mammal to utilize the sea water minerals, thus avoiding the reliance on foods ingested to accomplish this purpose. It is believed that the close association of the nutrient source with the sea water elements and minerals is necessary to achieve the maximum effectiveness of all of the sea water elements and minerals. This is particularly the case with the metabolizable carbohydrates.

Therefore, the present invention provides a nutritional solution for providing elements and minerals to a human or animal comprising a mixture of sea water elements and minerals in substantially the same proportion as in natural sea water or sea water diluted in an aqueous solution comprising water and at least one nutrient source. In particular embodiments, the nutrient source is a metabolizable carbohydrate or simple sugar selected from the group consisting of dextrose, glucose, fructose, galactose, and lactose. In a further embodiment, the aqueous solution further comprises one or more of the compounds selected from the group consisting of essential fatty acids, plant oils, animal oils, fish oils, antioxidants, antibiotics, pharmaceuticals, proteins, and amino acids. in particular embodiments, the present invention further comprises dietary fiber selected from the group consisting of soluble fiber, insoluble fiber, and mixtures thereof.

Preferably, the nutritional solution has an osmolality of between about 280 and 850 mOsms.

The nutritional solution is administered to the human or animal orally or the nutritional solution has an osmolality of between about 280 and 295 mOsms and is administered to the human or animal parenterally.

The present invention further provides a nutritional electrolyte solution which comprises in admixture (a) sea water elements and minerals in substantially the same proportion as in natural sea water or sea water in a physiologically acceptable aqueous solution of electrolytes; and (b) a metabolizable carbohydrate dissolved in the solution.

Preferably, the nutritional electrolyte solution has an osmolality of between about 280 and 850 mOsms.

In a further embodiment, the solution is an orally ingestible solution optionally including a flavoring and a nitrogen source. In a further embodiment, the solution is an intravenous solution optionally including a nitrogen source.

The present invention further provides a method for balancing electrolytes in and providing energy to a mammal, which comprises (a) administering an electrolyte solution which comprises in admixture (1) sea water elements and minerals in substantially the same proportion as in natural sea water or sea water in a physiologically acceptable aqueous solution of electrolytes; and (2) a metabolizable carbohydrate dissolved in the solution, so as to provide the energy and balance of electrolytes.

In particular embodiments, the solution is administered orally or the solution is administered intravenously. Preferably, the electrolyte solution has an osmolality of between about 280 and 850 mOsms.

The present invention further provides a dry composition in packaged form for dissolution in non-sea water to provide a nutritive solution which comprises (a) sea water elements and minerals in a physiologically acceptable form; and (b) a nutrient source. Preferably, the nutrient source comprises one or more of the compounds selected from the group consisting of essential fatty acids, plant oils, animal oils, fish oils, antioxidants, antibiotics, pharmaceuticals, carbohydrates, proteins, amino acids, dietary soluble fiber, and dietary insoluble fiber.

In particular embodiments, the composition is in a dosage unit form, preferably wherein the dosage unit is a tablet.

The present invention further provides a dry composition in packaged form for dissolution in non-sea water to provide a nutritional solution which comprises (a) sea water elements and minerals in a physiologically acceptable form; and (b) a metabolizable carbohydrate.

In particular embodiments, the composition is in a dosage unit form, preferably wherein the dosage unit is a tablet. Preferably, the dry composition further comprises one or more of the compounds selected from the group consisting of essential fatty acids, plant oils, animal oils, fish oils, antioxidants, antibiotics, pharmaceuticals, carbohydrates, proteins, amino acids, dietary soluble fiber, and dietary insoluble fiber.

The present invention provides a sterilized intravenous parenteral solution which comprises in admixture (a) sea water elements and minerals in substantially the same proportion as in natural sea water or sea water in a physiologically acceptable isotonic saline solution; and (b) a dextrose solution, wherein the parenteral solution contains about 1 to 4 parts by volume dextrose solution per part of the isotonic saline solution.

In a particular embodiment, the parenteral solution comprises 2 parts of a 5 to 10% by weight dextrose solution per part of the isotonic solution.

In a further embodiment, the parenteral solution contains sodium chloride, potassium chloride and magnesium sulfate. Preferably, the parenteral solution contains about 40 to 50 meq sodium chloride, 30 to 40 mEq of potassium chloride and 4 to 8 mEq of magnesium sulfate.

In a further embodiment, the parenteral solution in addition contains a protein hydrolyzate which provides nitrogen. Preferably, the protein hydrolyzate is prepared from a protein source selected from the group consisting of fibrin, whey, casein, egg albumin, soy, and meat.

In a preferred embodiment, the parenteral solution has an osmolality of between about 280 mOsms and 295 mOsms.

The present invention further provides a method of the treatment of a mammal in need of an intravenous parenteral solution which comprises (a) providing a sterilized intravenous parenteral solution which comprises in admixture sea water elements and minerals in substantially the same proportion as in natural sea water or sea water in an isotonic saline solution; and a dextrose solution, wherein the parenteral solution contains about 1 to 4 parts dextrose solution per part of the isotonic saline solution; and (b) injecting the solution intravenously into the mammal while the need exists.

In a further embodiment, the parenteral solution is antiviral and the injection continues to reduce a titer of the virus in the mammal. In a particular embodiment, the parenteral solution comprises 2 parts of a 5 to 10% by weight dextrose solution per part of the isotonic solution.

In a further embodiment, the parenteral solution contains sodium chloride, potassium chloride and magnesium sulfate. Preferably, the parenteral solution contains about 40 to 50 meq sodium chloride, 30 to 40 mEq of potassium chloride and 4 to 8 mEq of magnesium sulfate.

In a further embodiment, the parenteral solution in addition contains a protein hydrolyzate which provides nitrogen. Preferably, the protein hydrolyzate is prepared from a protein source selected from the group consisting of fibrin, whey, casein, egg albumin, soy, and meat.

In a preferred embodiment, the parenteral solution has an osmolality of between about 280 mosms and 295 mOsms. Preferably, the solution is filter sterilized.

The present invention further provides a fertilizer for plants which comprises in admixture (a) sea water elements and minerals in substantially the same proportion as in natural sea water or sea water in an aqueous solution; and (b) a nitrogen source. In particular embodiments, the fertilizer further comprises an herbicide, an insecticide, or both.

OBJECTS

It is an object of the present invention to provide nutritional compositions which comprise sea water elements and minerals in substantially the same proportion as in natural sea water or sea water along with a metabolizable nutrient source for administration to humans, animals, and plants.

It is a further object of the present invention to provide nutritional compositions comprising sea water elements and minerals in substantially the same proportions as they occur in natural sea water or sea water in an isotonic solution along with a metabolizable nutrient source which can be taken orally or parentally, in particular, intravenously or intramuscularly.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The present invention provides compositions which contain sea water or a mixture of sea water elements for oral or parenteral administration to humans and animals (mammals). Because all terrestrial life evolved from the sea, terrestrial organisms were designed to have a blood composition which comprises the elements and minerals of sea water in substantially the same amounts and proportions as they occur in sea water. However, because of depletion of the elements and minerals from the soil used for growing food and the inadequate nutrition of humans and animals (includes domestic and non-domestic mammals, aves, and reptiles) in general, humans and animals are not receiving the correct amounts and proportions of elements and minerals they need. In fact, many of the trace elements they need are completely lacking from the diet. As a consequence, humans and animals are susceptible to a variety of diseases and infections to which they would otherwise would be refractory to. Therefore, the nutritional compositions of the present invention are particularly useful as nutritional supplements which provide to the body the elements and minerals in sea water in substantially the same proportions as they occur in natural sea water. The nutrition provided by the sea water maintains or enhances the health status of the recipient human or animal.

In particular, the nutrition provided by the mixture of sea water elements and minerals or sea water enables the body to operate at its best performance, e.g., enables the immune system to function at peak performance or enables the various organ systems of the body to function at peak performance. As a consequence, a beneficial attribute of the present invention is that the mixture of sea water elements and minerals or sea water provide an effective means for inhibiting disease or infection in the recipient or facilitating the recipient's ability to fight a disease or infection.

For example, the nutritional compositions of the present invention can enable the recipient to overcome or repair damage caused by heart disease, cancer, diabetes, kidney disease, and the like. Since topically applying sea water to a wound appears to inhibit infection of the wound, it is believed that the nutritional compositions of the present invention comprising the mixture of sea water elements and minerals or sea water are antiviral and antibacterial. Therefore, in view of the above, the nutritional compositions of the present invention are expected to be useful when administered to patients infected with a disease causing agent such as anthrax, HIV, herpesvirus, smallpox, bubonic plague, and the like. Therefore, the nutritional compositions of the present invention are not only able to enhance the life of the recipient but is also able to extend the life span of the recipient.

Sea water is a solution of elements, minerals and gases, many of which are present in trace amounts. Sea water comprises at the least those elements and minerals which are shown in Table 1. of the elements and minerals in sea water, six elements and minerals make up over 99 percent of the dissolved solids in sea water. These major elements and minerals, which are present at over 100 ppm, are chloride (55.04%), sodium (30.61%), sulfate (7.68%), magnesium (3.69%), calcium (1.16%), and potassium (1.10%). Sodium ions and chloride ions, which join to make the mineral sodium chloride account for over 85 percent of these six elements.

Minor components in sea water are those elements and minerals present from 1 to 100 ppm. These minor elements and minerals include bromine (65%), carbon (28%), strontium (8%), boron (4.6%), silicon (3%), and fluorine (1%). The remainder of the elements and minerals in sea water are in trace amounts, concentrations of less than 1 ppm. At present, twenty-two of the elements and minerals in sea water are known to be essential to maintain life (Table 2).

TABLE 1

Average Composition of Sea Water[1]

| Element | ppm |
|---|---|
| Chlorine, Cl | 19,500 |
| Sodium, Na | 10,770 |
| Magnesium, Mg | 1,290 |
| Sulphur, S | 905 |
| Calcium, Ca | 412 |
| Potassium, K | 380 |
| Bromine, Br | 67 |
| Carbon, C | 28 |
| Nitrogen, N | 11.5 |
| Strontium, Sr | 8 |
| Oxygen, O | 6 |
| Boron, B | 4.4 |
| Silicon, Si | 2 |
| Fluorine, F | 1.3 |
| Argon, Ar | 0.43 |
| Lithium, Li | 0.18 |
| Rubidium, Rb | 0.12 |
| Phosphorus, P | 0.06 |
| Iodine, I | 0.06 |
| Barium, Ba | 0.02 |
| Molybdenum, Mo | 0.01 |
| Arsenic, As | 0.0037 |
| Uranium, U | 0.0032 |
| Vanadium, V | 0.0025 |
| Titanium, Ti | 0.001 |
| Zinc, Zn | 0.0005 |
| Nickel, Ni | 0.00048 |
| Aluminum, Al | 0.0004 |
| Cesium, Cs | 0.0004 |
| Chromium, Cr | 0.0003 |
| Antimony, Sb | 0.00024 |
| Krypton, Kr | 0.0002 |
| Selenium, Se | 0.0002 |
| Neon, Ne | 0.00012 |
| Manganese, Mn | 0.0001 |
| Cadmium, Cd | 0.0001 |
| Copper, Cu | 0.0001 |
| Tungsten, W | 0.0001 |
| Iron, Fe | 0.000055 |
| Xenon, Xe | 0.00005 |
| Zirconium, Zr | 0.00003 |
| Bismuth, Bi | 0.00002 |
| Niobium, Nb | 0.00001 |
| Thallium, Tl | 0.00001 |
| Thorium, Th | 0.00001 |
| Hafnium, Hf | $7 \times 10^{-6}$ |
| Helium, He | $6.8 \times 10^{-6}$ |
| Beryllium, Be | $5.6 \times 10^{-6}$ |
| Germanium, Ge | $5 \times 10^{-6}$ |
| Gold, Au | $4 \times 10^{-6}$ |
| Rhenium, Re | $4 \times 10^{-6}$ |
| Cobalt, Co | $3 \times 10^{-6}$ |
| Lanthanum, La | $3 \times 10^{-6}$ |
| Neodymium, Nd | $3 \times 10^{-6}$ |
| Lead, Pb | $2 \times 10^{-6}$ |
| Silver, Ag | $2 \times 10^{-6}$ |
| Tantalum, Ta | $2 \times 10^{-6}$ |
| Gallium, Ga | $2 \times 10^{-6}$ |
| Yttrium, Y | $1.3 \times 10^{-6}$ |
| Mercury, Hg | $1 \times 10^{-6}$ |
| Cerium, Ce | $1 \times 10^{-6}$ |
| Dysprosium, Dy | $9 \times 10^{-7}$ |
| Erbium, Er | $8 \times 10^{-7}$ |
| Ytterbium, Yb | $8 \times 10^{-7}$ |
| Gadolinium, Gd | $7 \times 10^{-7}$ |

TABLE 1-continued

Average Composition of Sea Water[1]

| Element | ppm |
|---|---|
| Praseodymium, Pr | $6 \times 10^{-7}$ |
| Scandium, Sc | $6 \times 10^{-7}$ |
| Tin, Sn | $6 \times 10^{-7}$ |
| Holmium, Ho | $2 \times 10^{-7}$ |
| Lutetium, Lu | $2 \times 10^{-7}$ |
| Thulium, Tm I | $2 \times 10^{-7}$ |
| Indium, In | $1 \times 10^{-7}$ |
| Trebium, Tb | $1 \times 10^{-7}$ |
| Palladium, Pd | $5 \times 10^{-8}$ |
| Samarium, Sm | $5 \times 10^{-8}$ |
| Tellurium, Te | $1 \times 10^{-8}$ |
| Europium, Eu | $1 \times 10^{-8}$ |
| Radium, Ra | $7 \times 10^{-11}$ |
| Protactinium, Pa | $5 \times 10^{-11}$ |
| Radon, Rn | $6 \times 10^{-16}$ |

[1]Note that the amounts of the elements in sea water varies depending on the analysis, where the sea water was obtained (proximity to land, rivers, etc.), and as more accurate analytical methods are used.
Data from Ocean Chemistry and Deep-Sea Sediments, Bearman (Ed.), Pergamon Press, Sydney, Australia (1989).

TABLE 2

Elements and Minerals Essential For Maintaining Life

| | |
|---|---|
| Calcium, Ca | Molybdenum, Mo |
| Chlorine, Cl | Nickel, Ni |
| Chromium, Cr | Phosphorus, P |
| Cobalt, Co | Potassium, K |
| Copper, Cu | Selenium, Se |
| Fluorine, F | Silicon, Si |
| Germanium, Ge | Sodium, Na |
| Iodine, I | Strontium, Sr |
| Iron, Fe | Sulphur, S |
| Magnesium, Mg | Vanadium, V |
| Manganese, Mn | Zinc, Zn |

Many of these elements and minerals are trace elements and minerals which need only be present in a few parts per million (ppm) concentration in order to provide or restore essential biological functions. In general, these trace elements and minerals are properly absorbed and utilized safely only when they occur in a ppm concentration. In some cases, larger quantities of these trace elements and minerals can be toxic. While sea water contains many other elements and minerals, mostly in trace amounts, at present, medical science has not recognized that these trace elements or minerals are also essential to maintain life. However, as our understanding of nutrition and health expands, it is expected that medical science will come to recognize that many, if not all, of these trace elements and minerals are important for maintaining nutrition and health, particularly when provided in substantially the proportions as they occur in natural sea water.

Certified reference material sea water preparations contain the elements and minerals shown in Table 3 and Table 4 provides a list of the major components of sea water.

TABLE 3

| Component | mg/kg (ppm) |
|---|---|
| Chlorine | 19,000 |
| Magnesium | 1,250 |
| Calcium | 400 |
| Bromide | 65 |
| Strontium | 12 |

TABLE 3-continued

| Component | mg/kg (ppm) |
| --- | --- |
| Silicon | 4 |
| Rubidium | 0.2 |
| Phosphorus | 0.1 |
| Iodine | 0.05 |
| Iron | 0.02 |
| Copper | 0.01 |
| Lead | 0.004 |
| Uranium | 0.0015 |
| Silver | 0.0003 |
| Chromium | 0.0003 |
| Nickel | 0.0001 |
| Mercury | 0.00003 |
| Sodium | 10,500 |
| Sulfur | 900 |
| Potassium | 380 |
| Carbon | 30 |
| Boron | 5 |
| Aluminum | 0.5 |
| Lithium | 0.1 |
| Barium | 0.05 |
| Arsenic | 0.02 |
| Manganese | 0.01 |
| Zinc | 0.005 |
| Selenium | 0.004 |
| Molybdenum | 0.0005 |
| Vanadium | 0.0003 |
| Cadmium | 0.0001 |
| Scandium | 0.00004 |
| Gold | 0.000006 |

Components and concentrations in Certified Reference Material sea water prepared by High Purity Standards, Inc. The components and concentrations are typically those present in sea water of 19.00% chlorinity.

TABLE 4

Average Concentrations of Several Major Components in Sea Water

| Component | g/kg |
| --- | --- |
| Chloride | 19.53 |
| Sodium | 10.76 |
| Sulfate | 2.72 |
| Magnesium | 1.294 |
| Calcium | 0.413 |
| Potassium | 0.387 |
| Bicarbonate | 0.142 |
| Bromide | 0.067 |
| Strontium | 0.008 |
| Boron | 0.004 |
| Fluoride | 0.001 |

Concentrations may vary due to depth, temperature, location, etc.

It is well known that for proper assimilation and utilization of many nutrients including elements or minerals, the nutrients must be provided in amounts and in proportion to each other which reflect their amounts and proportions as they occur in nature. In other words, when the nutrients are provided in their naturally occurring proportions, they are properly assimilated and utilized and their effect on maintaining or enhancing health is synergistic. In contrast, when the nutrients are provided in non-naturally occurring proportions or when particular nutrients are absent, assimilation and utilization is inefficient, ineffective, or in some cases toxic.

Therefore, the present invention provides nutritional compositions for maintaining and enhancing health in humans, animals (particularly mammals), and plants. The nutritional compositions comprise sea water minerals in substantially the same proportion as in natural sea water or sea water. Because the proportion of elements and minerals in sea water varies from location to location, the proportions are relative and will depend on the particular source for the sea water.

Preferably, the nutritional compositions comprise the sea water minerals or sea water in an isotonic solution, which preferably further includes a nutrient source or caloric source and optionally, a nitrogen source, protein hydrolyzates, vitamins, and other nutritionally or pharmaceutically acceptable compositions. Nutrient sources includes compounds or elements which are important to the quality of the cellular functions of the human or animal. Caloric sources include simple sugars such as sucrose, dextrose, glucose, lactose, maltose, galactose, arabinose, mannose, ribose, xylose, and fructose and carbohydrates which upon digestion yield glucose and other monosaccharides and include such macronutrients such as starch, maltodextrin, and hydrolyzed cereal solids. Protein hydrolyzates are mixtures of proteins, peptides and amino acids prepared from proteins such as soy, whey, casein, fibrin, egg albumin, and beef puree. Protein hydrolyzates can provide the source of nitrogen. Vitamins include the generally recognized vitamins A, $B_1$ (thiamin), $B_2$ (riboflavin), $B_6$ (pyridoxin), $B_{12}$ (colbalamins), C (ascorbic acid), D, E, and K ($K_1$ and $K_2$), folic acid, biotin, and niacin and provitamins such as betacarotenoids. Other nutritionally acceptable compositions include essential fatty acids and plant, animal, and fish oils, dietary soluble fiber, and dietary insoluble fiber. Pharmaceutically acceptable compositions include antibiotics and other pharmaceutically active compositions.

The nutritional compositions are useful for providing nutritional support in health care management, either in a medical environment or as over-the-counter nutritional supplements. The nutritional compositions are also useful as dietary supplements for inhibiting disease or infection in humans or animals or as dietary supplements for treatment of humans or animals with a disease or infection. Because the proportion of elements and minerals in sea water depends on the source of the sea water, compositions comprising sea water from particular locations or mixtures of sea water elements wherein the elements and minerals are in substantially the same proportion as they occur in the particular locations can vary as to their efficacy in maintaining or enhancing health.

Electrolyte solutions are used in vitro for use in tissue culture media, perfusion media, and incubation media as disclosed in U.S. Pat. No. 4,663,289 to Veech. Electrolyte solutions are also used in vivo in dietetic beverages such as SLIM FAST (Slim Fast Food Company, West Palm beach, Fla.), baby formulas such as the NESTLE CARNATION infant formulas (Nestle Corporation), and rehydration beverages such as those intended for use by persons engaged in athletic or other strenuous activities such as GATORADE (Stokely-Van Camp, Inc.) and those electrolyte solutions disclosed in U.S. Pat. No. 4,042,684 to Kahm, U.S. Pat. No. 4,322,407 to Ko, U.S. Pat. No. 4,592,909 to Winer et al., U.S. Pat. Nos. 4,981,687, 5,089,477, 5,147,650, and 5,238,684 all to Fregly et al., and U.S. Pat. No. 5,447,730 to Greenleaf.

Therefore, in one embodiment of the present invention, nutritional electrolyte solutions including but not limited to dietetic beverages, baby formulas, and rehydration beverages are provided which comprise electrolyte solutions comprising sea water elements and minerals prepared from sea water in substantially the same proportions as they occur in natural sea water, a mixture of certified ultrapure elements and minerals in substantially the same proportions as they occur in natural sea water, or sea water in a physiologically acceptable aqueous solution of electrolytes and a metabolizable carbohydrate dissolved in the solution.

As used herein electrolyte solutions further includes a solution comprising a mixture of sea water elements and minerals or sea water diluted in water (distilled, tap, spring, glacial, lake, spa, and the like) and a metabolizable carbohydrate. Preferably, the osmolality of the aforementioned electrolyte solutions is between about 280 mOsms and 850 mOsms.

In particular embodiments, the electrolyte solutions in the foregoing U.S. patents relating to electrolyte solutions comprise sea water elements and minerals from prepared from sea water in substantially the same proportions as they occur in natural sea water, a mixture of certified ultrapure elements and minerals in substantially the same proportions as they occur in natural sea water, or sea water wherein the proportion of components is adjusted to provide an electrolyte solution with a final osmolality between about 280 mOsms and 850 mOsms. The electrolyte solutions can be used in a method to balance the electrolytes in and providing energy to a human or mammal wherein the electrolyte solution are administered to the human or mammal orally or intravenously. The electrolyte solutions are also useful as a nutritional beverage to improve or maintain the health of a human or animal, particularly when administered daily.

The aforementioned electrolyte solutions of the present invention are an improvement over the electrolyte solutions of the prior art because they comprise the sea water elements and minerals in substantially the same proportion as they occur in natural sea water or sea water. It is the mixture of sea water elements and minerals in substantially the same proportions as they occur in natural sea water or sea water which enable the electrolyte solutions of the present invention to provide the proper amount of elements and minerals to a patient which imparts the unique health enhancing and health maintaining attributes of the electrolyte solutions of the present invention and which further provides the electrolyte solutions of the present invention with the ability to inhibit disease or infection or to facilitate cure of disease or infection.

Nutrition support is now recognized as an essential component of comprehensive healthcare management for critically stressed and malnourished patients. It is now known that early and proper nutrition support is beneficial in attenuating the adverse effects of a patient's metabolic response to injury or disease and in reducing the risks of morbid complications and even death. Depending on individual patients, situations, and circumstances, nutrients can be supplied through oral, enteral, and parenteral routes. Patients who have a functioning gastrointestinal tract, but cannot maintain adequate nutritional for a variety of reasons, are usually candidates for enteral nutrition wherein nutrition is provided by a feeding tube. Patients who have some form of gastrointestinal dysfunction are usually candidates for peripheral parenteral nutrition (PPN). Patients who are unable to obtain full nourishment through enteral or oral routes, total parenteral nutrition (TPN) support has been, and remains, a valuable therapy for promoting recovery and sustaining life.

For many years, the basic adult total parenteral nutrient solution, which was used when oral or enteral administration was not feasible, consisted of 165 g anhydrous dextrose in 860 ml of 5% dextrose in 5% fibrin hydrolyzate to which was added 40 to 50 mEq sodium chloride, 30 to 40 mEq potassium chloride, 4 to 8 mEq magnesium sulfate, and an appropriate amount of a multivitamin preparation (The Merck Manual, Twelfth Edition, Merck Research Laboratories, Rahway, N.J. pp. 1661-1663 (1972)). The preparation was then filter-sterilized. Thus, the basic requirements for TPN consisted of water, an energy source, nitrogen, vitamins, and the above several minerals in an isotonic saline solution. The basic requirements for TPN has not substantially been changed since then.

In general, medical science has determined that a parenteral solution should provide for every kg of body weight per day: 30 to 40 mL water; vitamins and essential minerals; 30 to 60 kcal of energy, the amount depending on whether the patient is a medical patient, a postoperative patient, or a hypercatabolic patient; and, 0.11 to 0.60 g (×6.25=protein), the amount depending on whether the patient is a medical patient, a postoperative patient, or a hypercatabolic patient. The energy requirements are increased by about 12% per ° C. fever.

In 1975, the American Medical Association, Department of Foods and Nutrition guidelines for trace essential elements in parental solutions recommended that the following four elements be added to parenteral solutions: zinc, copper, manganese, and chromium. Currently, the basic daily recommendations for TPN solutions include twelve elements: calcium, chloride, chromium, copper, iodine, magnesium, manganese, phosphorus, potassium, selenium, sodium, and zinc (The Merck Manual, Sixteenth Edition, Merck Research Laboratories, Rahway, N.J. Table 77-8, p. 947 (1992)).

TABLE 5

| Additives | Standard Solution | | | Heart Failure Sol. (low vol.-low Na+) | | |
|---|---|---|---|---|---|---|
| | Form Additives | Provided by Amino Acid Solution* | Final Content | Form Additives | Provided by Amino Acid Solution* | Final Content |
| Crys, a.a. 8.5% | 500 mL | | 4.25% | 300 mL | | 3.18% |
| NEPHRAMINE 5.4% | | | — | | | |
| Dextrose 50% | 500 mL | | 25% | | | — |
| Dextrose 70% | | | — | 500 mL | | 44% |
| Sodium (mEq) | 35 | 5 | 40 | — | 3 | 3 |
| Potassium (mEq) | 40 | — | 40 | 40 | — | 40 |
| Chloride | 35 | — | 35 | — | — | 0 |
| Calcium§ (mEq) | 4.6 | — | 4.6 | 4.6 | — | 4.6 |
| Phosphorus | 7 | 5 | 12 | 7 | 3 | 10 |
| **(mmol) | 8.1 | — | 8.1 | 8.1 | — | 8.1 |
| Magnesium†† (mEq) | 8.1 | — | 8.1 | 8.1 | — | 8.1 |
| Sulfate‡‡ (mEq) | 4.6 | — | 4.6 | 4.6 | — | 4.6 |
| Gluconate‡‡ (mEq) | 30 | 37 | 67 | 30 | 22.2 | 58.2 |
| Acetate‡‡ (mEq) | | | 1050 mL | | | 830 mL |
| Approx. Total Vol. | | | 42.5 | | | 25.4 |

TABLE 5-continued

| | | | |
|---|---|---|---|
| Amino acids (g) | | 6.5 | 3.9 |
| Nitrogen (g) | | 41 | 24 |
| Protein eq. (g)$^{\S\S}$ | | 850 | 1190 |
| Nonprotein cal (kcal)*** | | 0.81 | 1.4 |
| Caloric conc. (kcal/mL) | | | |

| | Low K$^+$-Low Na$^+$ Solution | | | Renal Failure Solution | | |
|---|---|---|---|---|---|---|
| Additives | Form Additives | Provided by Amino Acid Solution* | Final Content | Form Additives | Provided by Amino Acid Solution* | Final Content |
| Crys, a.a. 8.5% | 500 mL | | 4.25% | | | |
| NEPHRAMINE 5.4% | | — | | 500 mL | | 3.38% |
| Dextrose 50% | 500 mL | | 25% | | | |
| Dextrose 70% | | — | | 300 mL | | 26% |
| Sodium (mEq) | — | 5 | 5$^\dagger$ | ‡ | 3 | 3 |
| Potassium (mEq) | — | — | — | ‡ | — | — |
| Chloride | — | — | 0 | ‡ | — | — |
| Calcium$^\S$ (mEq) | 4.6 | — | 4.6 | ‡ | — | — |
| Phosphorus | 6 | 5 | 11 | ‡ | — | — |
| **(mmol) | 8.1 | — | 8.1 | ‡ | — | — |
| Magnesium$^{\dagger\dagger}$ (mEq) | 8.1 | — | 8.1 | ‡ | — | — |
| Sulfate$^{\ddagger\ddagger}$ (mEq) | 4.6 | — | 4.6 | ‡ | — | — |
| Gluconate$^{\ddagger\ddagger}$ (mEq) | — | 37 | 37 | ‡ | 22 | 22 |
| Acetate$^{\ddagger\ddagger}$ (mEq) | | | 1015 mL | | | 800 mL |
| Approx. Total Vol. | | | 42.5 | | | 27.0 |
| Amino acids (g) | | | 6.5 | | | 3.2 |
| Nitrogen (g) | | | 41 | | | 20 |
| Protein eq. (g)$^{\S\S}$ | | | 850 | | | 714 |
| Nonprotein cal (kcal)*** | | | 0.84 | | | 0.89 |
| Caloric conc. (kcal/mL) | | | | | | |

*Based on electrolyte content of FREAMINE III 8.5%
$^\dagger$Additional serum can be added as sodium chloride.
‡Additives only as indicated by serum levels.
$^\S$Added as calcium gluconate 0.46 mEq/mL.
**Added as potassium phosphate: K+ 4.4 mEq/mL, phosphorus 3 mmol/mL
$^{\dagger\dagger}$Added as magnesium sulfate 4.06 mEq/mL
$^{\ddagger\ddagger}$Not ordered by the physician; these anions balance the ordered cations.
$^{\S\S}$Based on 6.25 g protein per g nitrogen.
***Dextrose monohydrate provides 3.4 kcal/g.
From Table 77-9, The Merck Manual, 16$^{th}$ Edition Merck Research Laboratories, Rahway, New Jersey (1992), p. 948.

Table 5 shows several of the currently acceptable formulations of standardized TPN solutions to which vitamins and essential minerals are added. Because medical science is increasingly becoming more cognizant that elements and minerals are essential to proper nutrition, it is believed that in view of the present invention, subsequent recommendations for TPN solutions will include the sea water elements and minerals as taught herein.

In light of the above, the present invention provides parenteral solutions comprising the sea water elements and minerals in substantially the same proportions as they occur in natural sea water or sea water. Preferably, the parenteral solution further comprises an caloric source such as dextrose or other simple sugar, a physiologically acceptable isotonic saline solution, and a nitrogen source. The nutrition provided by mixture of sea water elements and minerals or the sea water enables the body to operate at its best performance, e.g., enable the immune system to function at peak performance or enable the organ systems of the body to function at peak performance. As a consequence, a beneficial attribute of the present invention is that the parenteral solutions comprising mixture of sea water elements and minerals or the sea water provide an effective means for inhibiting disease or infection in a patient receiving the parenteral solution or facilitating the patient's ability to fight a disease or infection. For example, the parenteral solutions of the present invention can enable the patient to overcome or repair damage caused by heart disease, cancer, diabetes, kidney disease, and the like. Since topically applying sea water to a wound appears to inhibit infection of the wound, it is believed that the parenteral solutions comprising mixture of sea water elements and minerals or sea water are antiviral and antibacterial. Therefore, in view of the above, the parenteral solutions of the present invention are expected to be useful when administered to patients infected with a disease causing agent such as anthrax, HIV, herpesvirus, and the like.

To prepare the parenteral solution comprising the sea water elements and minerals, sea water is filter sterilized to remove debris and other contaminants. The sea water is not heat sterilized because heat can adversely alter the composition of the sea water. For example, sea water contains various gases dissolved therein which are released upon heating and various minerals in the sea water decompose at temperatures normally used to heat sterilize. Alternatively, sea water can be filtered to remove debris and other contaminants and the filtered sea water sterilized by irradiation to produce the sterile sea water.

The sterile sea water is then added to a parenteral solution, preferably a parenteral solution with a composition substantially similar to the composition of one of the parenteral solutions in Table 5. The amount of sea water that is added is an amount which does not alter the osmolality of the parenteral solution to an osmolality that would be incompatible to the patient. In general, an osmolality of between about 280 mOsms and 295 mOsms is considered isotonic with human serum and tissues and would be acceptable for a parenteral solution. Therefore, the amounts of particular components of the parenteral solutions of Table 5 are appropriately reduced to ensure that the parenteral solution comprising the sea water has an osmolality of between about 280 mOsms and 295 mOsms.

As another example, the parenteral solution comprising the sea water elements and minerals is prepared as follows. Sea water is diluted with sterile distilled water containing a caloric source to provide a parenteral solution with a final osmolality of between about 280 mOsms and 295 mOsms. One part sea water to 2.2 parts distilled water containing the caloric source provides a parenteral solution with an osmolality of between about 280 mOsms and 295 mOsms. The parenteral solution can further contain any combination of vitamins; amino acids; antibiotics; pharmaceuticals; essential fatty acids; plant, animal, or fish oils; antioxidants; and the like, in amounts that do not alter the final osmolality of the parenteral solution from between about 280 mOsms and 295 mOsms.

The parenteral solution comprising sea water elements and minerals is also prepared using a dried mixture of the sea water elements and minerals. Sea water, which is filtered to remove debris and other contaminants, is gently evaporated without application of high temperatures to provide a dried mixture of the sea water elements and minerals. Gentle evaporation of the sea water produces wet crystals which contain the elements and minerals of the sea water, including the gases dissolved therein, in substantially the proportion they occur in natural sea water. Because high temperatures will destroy many of the minerals and elements in the sea water, a preferred method for preparing the dried mixture of minerals and elements from sea water is to use a method substantially similar to the ancient methods used to produce salt from sea water such as those methods used by the Celts or Phoenicians. For example, the method used to produce Brittany Celtic sea salt, or more preferably, the method used to prepare Brittany Fleur De Sel De Guérande, are used to produce the dried mixture of elements and minerals from sea water. The parenteral solution containing the sea water elements and minerals is prepared by adding the dried mixture of sea water elements and minerals to any one of the parenteral solutions in Table 5 to produce the parenteral solution comprising the sea water elements and minerals with a final osmolality of between about 280 mOsms and 295 mOsms.

As another example, the parenteral solution comprising sea water elements and minerals can be prepared from the dried mixture of sea water elements and minerals by dissolving the sea water elements and minerals in sterile distilled water containing a caloric source to provide a parenteral solution with a final osmolality of between about 280 mosms and 295 mOsms. The parenteral solution can further contain any combination of vitamins; amino acids; antibiotics; pharmaceuticals; essential fatty acids; plant, animal, or fish oils; antioxidants; and the like, in amounts that do not alter the final osmolality of the parenteral solution from between about 280 mOsms and 295 mOsms.

In a further embodiment of the parenteral solution comprising sea water elements and minerals, the parenteral solution is made by mixing a solution, which contains certified ultrapure minerals and elements in distilled water in substantially the same proportions as they occur in natural sea water, with a parenteral solution in Table 5, or with distilled water containing a caloric source, and filter sterilizing to produce the parenteral solution comprising sea water elements and minerals. The final osmolality of the parenteral solution is between about 280 mOsms and 295 mOsms. The parenteral solution can further contain any combination of vitamins; amino acids; antibiotics; pharmaceuticals; essential fatty acids; plant, animal, or fish oils; antioxidants; and the like, in amounts that do not alter the final osmolality of the parenteral solution from between about 280 mOsms and 295 mOsms. In this embodiment, parenteral solutions comprising particular combinations of sea water elements and minerals are made. For example, parenteral solutions can be made which contain the sea water elements and minerals recited in Table 1, Table 2, Table 3, or Table 4 or subsets of the sea water elements and minerals recited in the tables.

In a particular embodiment of the filter sterilized parenteral solution comprising sea water or the sea water elements and minerals in substantial proportion to that which occurs in natural sea water, the parenteral solution comprises 2 parts of 5 to 10% dextrose or other simple sugar in water to 1 part of isotonic solution of between about 280 mOsms and 295 mOsms containing an appropriate quantity of the mixture of sea water elements and minerals or sea water. An appropriate amount of mixture of elements and minerals or the sea water depends on the body weight of the patient and the purpose for providing the patient a parenteral solution containing sea water, e.g., for general nutrition, inhibiting disease or infection, treatment of a disease or infection. Therefore, in some cases, it will be necessary to supplement the solution of sea water elements and minerals or sea water with saline to produce the isotonic solution of between about 280 mOsms and 295 mOsms.

In further embodiments of the above parenteral solution comprising the sea water elements and minerals in substantial proportion to that which occurs in natural sea water or sea water, the parenteral solution further includes amino acids and vitamins. The amino acids can be provided as a fibrin, whey, soy, meat, or other protein hydrolyzate or as a mixture comprising certified ultrapure amino acids.

The aforementioned parental solutions of the present invention are an improvement over the parenteral solutions of the prior art because they comprise the sea water elements and minerals in substantially the same proportion as they occur in natural sea water or sea water. It is the mixture of sea water elements and minerals or sea water which enable the parenteral solutions of the present invention to provide the proper amount of elements and minerals to a patient which imparts the unique health enhancing and health maintaining attributes of the parenteral solutions of the present invention and which further provides the parenteral solutions of the present invention with the ability to inhibit disease or infection or to facilitate cure of disease or infection.

In a further embodiment of the present invention, elemental (chemically defined) diets are provided which comprises filter sterilized solution of sea water elements and minerals prepared from sea water in which the elements and minerals are in substantially the same proportions as they occur in natural sea water, solution of a mixture of certified ultrapure elements and minerals in substantially the same proportions as they occur in natural sea water, or sea water. Elemental diets are frequently given internally to patients who are on modified consistency diets, the chronically ill with anorexia, and those patients with chronic inflammatory and malignant disease. The elemental diets provide essential nutrients in a readily assimilated form, require little or no active digestion, and have minimal residue.

Elemental diets are generally prepared commercially and include, but not limited to, such commercially available products as COMPLEAT (Novartis Nutrition Corporation, Minneapolis, Minn.), SUSACAL (Mead Johnson & Company, a division of Bristol Myers Squibb Company, Evansville, Ind.), ISOCAL (Mead Johnson & Company), ENSURE (Ross Laboratories, a division of Abbott Laboratories, Abbott park, Ill.), AMIN-AID (McGraw Pharmaceutical Company, a division of McGraw-Hill Companies), TRAVASORB (Clintec Nutrition Company, a division of Baxter Corporation, Deerfield, Ill.), and TRAUMA-CAL (Mead Johnson & Company). In general, these elemental diets include either some or all of the following elements or minerals: calcium, chloride, chromium, copper, iron, iodine, magnesium, manganese, molybdenum, phosphorus, selenium, and zinc or as is the case for AMIN-AID, no elements and minerals (The Merck Manual, Sixteenth Edition, Merck Research Laboratories, Rahway, N.J. Table 77-5, pp. 943-944 (1992)).

Because the elemental diets of the present invention comprise filter sterilized solution of sea water elements and minerals prepared from sea water wherein the elements and minerals are in substantially the same proportions as they occur in natural sea water, a solution of a mixture of certified ultrapure elements and minerals in substantially the same proportions as they occur in natural sea water, or sea water, the elemental diets of the present invention are an improvement over the elemental diets of the prior art. Preferably, the elemental diets of the present invention comprise a commercially available elemental diet formulations wherein the minerals comprising the commercially available elemental diet, a portion of the water comprising the commercially available elemental diet, or both is replaced with filter sterilized sea water, filter sterilized solution containing the sea water elements and minerals prepared from sea water in wherein the elements and minerals are in substantially the same proportions as they occur in natural sea water, or a solution of certified ultrapure elements and minerals in substantially the same proportions as they occur in natural sea water.

In the case where a solution of certified ultrapure elements and minerals in substantially the same proportions as they occur in natural sea water is used to make the elemental diet, the elements and minerals can include any combination of the elements and minerals recited in Table 1, Table 2, Table 3, or Table 4. In further embodiments, the elemental diet can further include any one or more of the following: essential fatty acids; plant, animal, or fish oils; antioxidants; antibiotics; pharmaceuticals; dietary soluble fiber; dietary insoluble fiber; and the like. Preferably, the osmolality of the elemental diet is between about 280 mOsms and 850 mOsms.

The aforementioned elemental diets of the present invention are an improvement over the elemental diets of the prior art because they comprise the sea water elements and minerals in substantially the same proportion as they occur in natural sea water or sea water. It is the mixture of sea water elements and minerals in substantially the same proportions as they occur in natural sea water or sea water which enable the elemental diets of the present invention to provide the proper amount of elements and minerals to a patient which imparts the unique health enhancing and health maintaining attributes of the elemental diets of the present invention and which further provides the elemental diets of the present invention with the ability to inhibit disease or infection or to facilitate cure of disease or infection.

In a further embodiment of the present invention, dry compositions in packaged form for dissolution in non-sea water to provide a nutritional solution are provided which comprise a dried mixture of the elements and minerals in sea water in substantially the same proportions as they occur in natural sea water and a metabolizable carbohydrate or simple sugar and/or at least one nutrient source such as vitamins; proteins; amino acids; essential fatty acids; and, plant, animal, or fish oils, preferably in a physiologically acceptable form. In further embodiments of the dry composition, the composition further includes any one or more of the following: fillers, binders, flavorings, antioxidants, antibiotics, other pharmaceuticals, dietary soluble fiber, dietary insoluble fiber, and the like. The composition is preferably in a dosage form which can be a granulated powder, capsule containing the granulated powder, or a tablet. The dry compositions are useful as nutritional supplements to improve or maintain the health of a human or animal, particularly when administered either dry or dissolved in an aqueous solution or water to the human or animal, particularly when administered daily.

In general, the dried mixture of elements and minerals are prepared by filtering the sea water to remove debris and other contaminants and removing the water by gentle evaporation without the application of high temperatures. A preferred method for preparing the mixture of minerals and elements from sea water is to use a method substantially similar to the ancient methods used to produce salt from sea water. For example, the method used to produce Brittany Celtic sea salt, or more preferably, the method used to prepare Brittany Fleur De Sel De Guérande, are used to produce the dried mixture of elements and minerals from sea water. The dried mixture of elements and minerals prepared from the sea water is used to make the dry composition which can stored as a granulated powder, formed into tablets, or packed into capsules.

In a further alternative, the dry composition is prepared from certified ultrapure elements and minerals wherein the proportion of the elements and minerals in the dry composition is in substantially the same proportions as they occur in natural sea water. The elements and minerals can include all or any combination of the elements and minerals recited in Table 1, Table 2, Table 3, or Table 4. The mixture of ultrapure elements and minerals is used to make the dry composition.

The dry compositions of the present invention provide a convenient means for providing a nutritional solution containing sea water elements and minerals in substantially the same proportion as they occur in natural sea water to a human or an animal. The dry compositions can be taken orally or dissolved in a liquid which is then taken orally or filtered sterilized and administered intravenously. It is the mixture of sea water elements and minerals which enable the dry compositions of the present invention to provide the proper amount of elements and minerals to a patient which imparts the unique health enhancing and health maintaining attributes of the dry compositions of the present invention and which further provides the dry compositions of the present invention with the ability to inhibit disease or infection or to facilitate cure of disease or infection.

The present invention further provides fertilizing solutions for maintaining the health of plants comprising sea water, a mixture of sea water elements and minerals in substantially the same proportions as they occur in natural sea water, or a mixture of certified ultrapure elements and minerals in substantially the same proportions as they occur in natural sea water in an aqueous solution containing plant nutrients. The fertilizing solutions are used to fertilize agricultural plants, garden plants, and house plants. Prior art fertilizers produced from sea water such as those disclosed in U.S. Pat. No. 4,015,971 to Barannik are prepared by precipitating micro-elements and organic substances present in the sea water and using the precipitated micro-elements and organic substances as a fertilizer. However, unlike the fertilizing solutions of the present invention which contains substantially all the sea water elements and minerals in substantially the same proportions as they occur in natural sea water, the prior art fertilizers do not contain substantially all the elements and minerals of sea water in the same proportions as they occur in natural sea water. For example, in the case of the '971 patent, which uses iron ions to precipitate the micro-elements and organic substances, the fertilizers so produced contain about 34 to 31.5% iron, which is considerably more iron than which occurs naturally in sea water.

The following examples are intended to promote a further understanding of the present invention.

EXAMPLE 1

The following example illustrates a nutritional solution for providing elements and minerals orally to an animal or human.

Sea water is obtained from the Catalina Gulf, California, and filtered without heat (Natural Sources, Long beach, Calif. is commercial source for Catalina Gulf sea water). The sea water is diluted with sterile distilled water at a ratio of 1 part sea water to 2 parts sea water to provide the nutritional solution for oral consumption by humans or animals. The solution can further include an energy source, vitamins, and particular electrolytes.

EXAMPLE 2

The following example illustrates that a fertilizing solution of the present invention can be provided to house plants.

The sea water is obtained from the Catalina Gulf, California, and filtered without heat (Natural Sources, Long beach, Calif.). The sea water is diluted 1:2 with sterile distilled water and then mixed with sugar and plant nutrients to produce the fertilizing solution. The fertilizing solution comprising the sea water is administered to the house plants by watering.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

We claim:

1. A sterilized intravenous parenteral solution which comprises in admixture:

(a) elements and minerals in natural sea salt for human consumption, consisting essentially of:

| Component | mg/kg (ppm) |
|---|---|
| Chlorine | 19,000 |
| Magnesium | 1,250 |
| Calcium | 400 |
| Bromide | 65 |
| Strontium | 12 |
| Silicon | 4 |
| Rubidium | 0.2 |
| Phosphorus | 0.1 |
| Iodine | 0.05 |
| Iron | 0.02 |
| Copper | 0.01 |
| Lead | 0.004 |
| Uranium | 0.0015 |
| Silver | 0.0003 |
| Chromium | 0.0003 |
| Nickel | 0.0001 |
| Mercury | 0.00003 |
| Sodium | 10,500 |
| Sulfur | 900 |
| Potassium | 380 |
| Carbon | 30 |
| Boron | 5 |
| Aluminum | 0.5 |
| Lithium | 0.1 |
| Barium | 0.05 |
| Arsenic | 0.02 |
| Manganese | 0.01 |
| Zinc | 0.005 |
| Selenium | 0.004 |
| Molybdenum | 0.0005 |
| Vanadium | 0.0003 |
| Cadmium | 0.0001 |
| Scandium | 0.00004 |
| Gold | 0.000006 | in a physiologically acceptable isotonic saline solution; and (b) a dextrose solution, wherein the parenteral solution contains about 1 to 4 parts by volume dextrose solution per part of the isotonic saline solution, wherein the parenteral solution has an osmolality of between about 280 mOsms and 295 mOsms.

2. The parenteral solution of claim 1 wherein there are 2 parts of a 5 to 10% by weight dextrose solution per part of the isotonic solution.

3. The parenteral solution of claim 1 containing sodium chloride, potassium chloride and magnesium sulfate.

4. The parenteral solution of claim 3 containing about 40 to 50 meq sodium chloride, 30 to 40 mEq of potassium chloride and 4 to 8 mEq of magnesium sulfate.

5. The parenteral solution of claim 4 which in addition contains a protein hydrolyzate which provides nitrogen.

6. The parenteral solution of claim 1 wherein the solution in addition consists essentially of amino acids which provide total parenteral nutrition.

7. A method of the treatment of a mammal in need of an intravenous parenteral solution which comprises:

(a) providing a sterilized intravenous parenteral solution which comprises in admixture:

elements and minerals in natural sea salt for human consumption, consisting essentially of:

| Component | mg/kg (ppm) |
|---|---|
| Chlorine | 19,000 |
| Magnesium | 1,250 |
| Calcium | 400 |
| Bromide | 65 |
| Strontium | 12 |
| Silicon | 4 |
| Rubidium | 0.2 |
| Phosphorus | 0.1 |
| Iodine | 0.05 |
| Iron | 0.02 |
| Copper | 0.01 |
| Lead | 0.004 |
| Uranium | 0.0015 |
| Silver | 0.0003 |
| Chromium | 0.0003 |
| Nickel | 0.0001 |
| Mercury | 0.00003 |
| Sodium | 10,500 |
| Sulfur | 900 |
| Potassium | 380 |
| Carbon | 30 |
| Boron | 5 |
| Aluminum | 0.5 |
| Lithium | 0.1 |
| Barium | 0.05 |
| Arsenic | 0.02 |
| Manganese | 0.01 |
| Zinc | 0.005 |
| Selenium | 0.004 |
| Molybdenum | 0.0005 |
| Vanadium | 0.0003 |
| Cadmium | 0.0001 |

-continued

| Component | mg/kg (ppm) |
|---|---|
| Scandium | 0.00004 |
| Gold | 0.000006 | in an isotonic saline solution; and a dextrose solution, wherein the parenteral solution contains about 1 to 4 parts dextrose solution per part of the isotonic saline solution, wherein the parenteral solution has an osmolality of between about 280 mOsms and 295 mOsms; and (b) injecting the solution intravenously into the mammal while the need exists.

8. The method of claim 7 wherein there are 2 parts of a 5 to 10% by weight dextrose solution per part of the isotonic solution.

9. The method of claim 7 wherein the solution contains sodium chloride, potassium chloride and magnesium sulfate.

10. The method claim 9 containing about 40 to 50 mEq sodium chloride, 30 to 40 mEq of potassium chloride and 4 to 8 mEq of magnesium sulfate.

11. The method of claim 7 which in addition contains a protein hydrolyzate which provides nitrogen.

12. The method of claim 7 wherein the solution in addition comprises amino acids which provide total parenteral nutrition.

13. The method of claim 7 wherein the solution is filter sterilized.

* * * * *